(12) United States Patent
Kerley et al.

(10) Patent No.: US 7,906,702 B2
(45) Date of Patent: Mar. 15, 2011

(54) CATEGORICALLY RANKING ANIMALS FOR FEED EFFICIENCY

(75) Inventors: Monty S. Kerley, Columbia, MO (US); William Kolath, Calgary (CA); Joseph Golden, Mountain Grove, MO (US)

(73) Assignee: The University of Missouri System, Columbia, MO (US)

( * ) Notice: Subject to any disclaimer, the term of this patent is extended or adjusted under 35 U.S.C. 154(b) by 1106 days.

(21) Appl. No.: 11/619,842

(22) Filed: Jan. 4, 2007

(65) Prior Publication Data

US 2007/0186297 A1    Aug. 9, 2007

Related U.S. Application Data

(60) Provisional application No. 60/756,439, filed on Jan. 5, 2006.

(51) Int. Cl.
*A61K 67/027* (2006.01)
*C12Q 1/00* (2006.01)
*C12Q 1/26* (2006.01)
*C12Q 1/68* (2006.01)

(52) U.S. Cl. ............... 800/15; 435/4; 435/6; 435/25

(58) Field of Classification Search .............. None
See application file for complete search history.

(56) References Cited

U.S. PATENT DOCUMENTS

| | | | |
|---|---|---|---|
| 6,805,075 B2 | 10/2004 | Pratt | 119/51.02 |
| 6,868,804 B1 | 3/2005 | Huisma et al. | 119/842 |
| 7,199,281 B2 * | 4/2007 | Murray et al. | 800/25 |
| 7,256,283 B2 | 8/2007 | Kriz et al. | 536/24.1 |
| 7,256,324 B2 | 8/2007 | Conner et al. | 800/287 |
| 2007/0209084 A1 * | 9/2007 | Collier et al. | 800/15 |

FOREIGN PATENT DOCUMENTS

| | | |
|---|---|---|
| WO | WO 96/35127 | 7/1996 |
| WO | WO 03/032234 | 4/2003 |

OTHER PUBLICATIONS

Basarab et al., "Residual feed intake and body composition in young growing cattle," *Can. J. Anim. Sci*, 83:189-204, 2003.
Bottje et al., "Association of mitochondrial function with feed efficiency within a single genetic line of male broilers," *Poultry Sci.*, 81:546-555, 2002.
Bottje et al., "Role of mitochondria in phenotypic expression of feed efficiency," *J. Appl. Poult. Res.*, 13:94-105, 2004.
Chance et al., "Hydroperoxide metabolism in mammalian organs," *Physiol. Rev.*, 59:527-605, 1979.
Crews, "Genetics of efficient feed utilization and national cattle evaluation: a review," *Genet. Mol. Res.*, 4:152-165, 2005.
Fox et al., "Identifying differences in efficiency in beef cattle," Animal Science Department, Mimeo 225, Cornell University, Ithaca, NY, 2004.
Herd et al., "Reducing the cost of beef production through genetic improvement in residual feed intake: opportunity and challenges to application," *J. Anim. Sci.*, 81:E9-E17, 2003.
Hersom et al., "Effect of live weight gain of steers during winter grazing: III. Blood metabolites and hormones during feedlot fmishing[1, 2]," *J. Anim. Sci.*, 82:2059-2068, 2004.
Iqbal et al., "Low feed efficient broilers within a single genetic line exhibit higher oxidative stress and protein expression in breast muscle with lower mitochondrial complex activity," *Poultry Sci.*, 83:474-484, 2004.
Johnson et al., "The history of energetic efficiency research: where have we been and where are we going," *J. Anim. Sci.*, 81:E27-E38, 2003.
Kneeland et al., "Identification and fine mapping of quantitative trait loci for growth traits on bovine chromosomes 2, 6, 14, 19, 21, and 23 within one commercial line of Bos taurus[1]," *J. Anim. Sci.*, 82:3405-3414, 2004.
Lutz et al., "Quantitative relationship between mitochondrial bioenergetics and efficiency of animal growth," *J Anim. Sci.* 81(Suppl. 1):141, (Abstr.), 2003.
Moore et al., "Genetic and phenotypic relationships between insulin-like growth factor-I (IGF-I) and net feed intake, fat, and growth traits in Angus beef cattle," *Aust. J. Agr. Res.*, 56:211-218, 2005.
Nkrumah et al., "Different measures of energetic efficiency and their phenotypic relationships with growth, feed intake, and ultrasound and carcass merit in hybrid cattle," *J. Anim. Sci.*, 82:2451-2459, 2004.
Ojano-Dirain et al., "Determination of mitochondrial function and site-specific defects in electron transport in duodenal mitochondria in broilers with low and high feed efficiency," *Poultry Sci.*, 83:1394-1403, 2004.
Sandelin et al., "Assessment of respiratory chain complex activities and electron transport chain protein expression in muscle mitochondria in Angus steers with low and high feed efficiency," *J. Anim. Sci.*, 82(Suppl. 1):416 (Abstr.), 2004.
Yambayamba et al., "Hormonal status, metabolic changes, and resting metabolic rate in heifers undergoing compensatory growth," *J. Anim. Sci.*, 74:57-69, 1996.

* cited by examiner

*Primary Examiner* — Herbert J. Lilling
(74) *Attorney, Agent, or Firm* — SNR Denton US LLP

(57) ABSTRACT

The invention provides methods for managing livestock for breeding or production based on one or more measurements of mitochondrial function. Measurement of mitochondrial function may also be correlated with a calculated or known feed efficiency of livestock animals to yield a predicted feed efficiency for the animal. The invention overcomes deficiencies associated with phenotypic assays for predicted breeding and production value.

9 Claims, No Drawings

CATEGORICALLY RANKING ANIMALS FOR FEED EFFICIENCY

This application claims benefit of and priority to U.S. Provisional Patent Application 60/756,439, filed Jan. 5, 2006, which is herein incorporated by reference in its entirety.

The United States Government may own certain rights in the invention pursuant to USDA CSREES Grant No. 2004-34450-14578.

BACKGROUND OF THE INVENTION

1. Field of the Invention

The present invention relates generally to the field of animal breeding and the production of animal food products. More particularly, it concerns methods for ranking and selecting animals for feed efficiency.

2. Description of Related Art

Little genetic improvement for meat quality or the efficiency of production has occurred in beef cattle populations in the last 100 years, despite development of Selection Index theory over 60 years ago (Hazel, 1943). This is due at least in part to the little information available on which to make selection decisions to improve these traits. It is time consuming, difficult, and costly to obtain carcass information in commercial packing plants and to retain the identity of individual animals. Thus, little information is available upon which to make breeding decisions to improve the net efficiency of growth. Considerable efforts have been expended to develop live animal ultrasound techniques to provide indirect measures of carcass traits. Due to the importance of these traits and their cost and difficulty of measurement, there is a great need for development of measures for selection of beneficial traits in beef cattle such as diagnostic methods based on biochemical and genetic markers. Such techniques could greatly increase the productivity of breeding programs and eliminate the need for costly or ineffective phenotypic selections.

Expected Progeny Differences (EPD), a genetic evaluation tool, have gained increasing use in cattle breeding. Many purebred beef and dairy cattle organizations now conduct yearly evaluations that calculate EPD for a number of cattle weight, growth, and production traits with economic importance, including birth weight, weaning weight, ribeye area, and others. However, an EPD for feed efficiency or a trait that is strongly correlated with feed efficiency has not yet been developed, in part because a recognized standard for "efficiency" has been lacking. Efficiency may be defined in a number of ways. Ratios of inputs and outputs, such as gain to feed (G:F) or feed to gain (F:G), also termed the "Feed Conversion Ratio" (FCR), have been used. However, as noted below, these ratios can confound growth rate, body size, and appetite with metabolic efficiency.

One promising approach for developing a feed efficiency EPD involves Residual Feed Intake (RFI), sometimes called net feed intake. RFI is defined as the difference between an animal's actual feed intake and its expected feed requirements for maintenance and growth. Thus, it is the variation in feed intake between animals that remains after requirements for maintenance and growth have been removed. Expected feed intake is calculated based on the statistical model $$Y=\beta_0+\beta_1 X1+\beta_2 X2+\epsilon,$$

wherein Y is expected feed intake; $\beta_0$ is a regression intercept; $\beta_1$ is the partial regression of daily feed intake on average daily gain (ADG); X1 is Average Daily Gain; $\beta_2$ is the partial regression of daily intake on body weight; X2 is body weight; and $\epsilon$ is the random error. The body weight of the animal is typically expressed as the midweight during test (sometimes transformed to a "metabolic midweight" by raising the midweight to about the power of 0.75, e.g. $kg^{0.75}$; Crews 2005). The RFI for an animal is calculated as actual feed intake minus expected intake (Y). The mean RFI for a tested population is zero. Efficient animals, with an RFI below zero, have daily feed intakes below what would have been predicted given their levels of production or body weight.

Importantly for breeding purposes, RFI has been found to exhibit moderate genetic heritability. However, given the phenotypic way in which it is calculated, the underlying biochemical and genetic factors that result in a given RFI have been unclear. RFI has typically been calculated by an expensive and time consuming phenotypic process, wherein cattle are subjected to a feeding regimen, and their individual feed intake and growth are closely followed, typically over a more than 70 day period, for instance, in conjunction with use of a feed management system like the GrowSafe® Feed Intake System (U.S. Pat. No. 6,868,804), or other cattle management system (e.g. U.S. Pat. No. 6,805,075), in order to obtain data on their feed intake and growth. Significantly, RFI may be used as a selection tool that does not confound metabolic efficiency with growth rate.

Johnson et al. (2003) and Herd et al. (2003) discussed dietary energy use research in beef cattle production in general, including the use of calculated RFI as an efficiency measurement. Basarab et al. (2003) reported differences in average daily feed intake (ADFI) and G:F (gain to feed ratio) when steers grouped according to their calculated RFI were compared. Basarab also reported increased fat deposition in steers selected to have high RFI. However, mitochondrial function was not examined. Nkrumah et al. (2004) reported on the relationship between RFI and other measures of energetic efficiency and growth in cattle. However, no underlying mechanism to account for variations in RFI between animals was demonstrated.

Moore et al (2005) found that insulin-like growth factor (IGF) was correlated to residual feed intake (genetic correlation of 0.35). The less efficient cattle had higher IGF levels, as would be expected since these cattle consume more feed without increased levels of gain. Use of this approach to select or predict cattle for feed efficiency can however be influenced by the feeding management scheme of the calf, and is not as highly correlated to RFI as mitochondrial respiration rate. Owens et al. (1996; WO96/35127) also describe selection of livestock (e.g. pigs) based on IGF levels.

Bottje and coworkers (Bottje et al. 2002; Iqbal et al., 2004; Ojano-Dirain et al., 2004; WO03/032234) describe aspects of mitochondrial function, including level of reactive oxygen species production, that may be used to select for "feed efficiency" (FE) in broiler chicks. They reported that activity of mitochondrial complexes I and II was positively correlated with FE in broiler chicks. That is, high FE birds had higher respiratory chain complex activities than lower FE birds. However, Bottje and coworkers did not use RFI as a measurement of feed efficiency. Rather, their definition of FE, e.g. as a ratio consisting of the weight gain of an animal divided by the weight of feed consumed (G:F), or its inverse (F:G), confounds several underlying variables, including growth rate, body size, and appetite, with the metabolic efficiency of feed use, per se.

Bottje and coworkers (e.g. Bottje et al., 2002; Iqbal et al., 2004; Ojano-Dirain et al., 2004) reported increased weight gain for chickens displaying high feed efficiency, with no difference in feed intake between high and low feed efficient birds, and have also reported that isolated mitochondria of low feed efficient chickens generated greater amounts of hydrogen peroxide than did mitochondria of high feed efficiency birds. Lutz and Stahly (2003) have also described evidence of a link between inefficient mitochondrial respiration and decreased G:F in rats.

Sandelin et al. (2004) reported that activities of respiratory chain Complex I and II were higher in low FE steers than in high FE steers. They also use G:F as their measure of FE. The result in cattle apparently contradicts the work of Bottje et al., above in chickens. Thus, the relationship of mitochondrial function as measured by mitochondrial protein activities, rate of electron flux through the electron transport chain, and correlation to FE (however defined) in animals is unclear.

SUMMARY OF THE INVENTION

In one aspect, the invention provides a method for predicting metabolic efficiency in a first livestock animal comprising assaying the function of mitochondria of the first livestock animal and correlating the function with the mitochondrial function and feed efficiency of at least a second livestock animal to obtain a predicted metabolic efficiency for said first livestock animal. In certain embodiments, feed efficiency may be determined by Residual Feed Intake. In other embodiments, assaying the function of mitochondria of the first livestock animal comprises assaying at least one characteristic selected from the group consisting of oxygen consumption rate, Complex I electron transport rate, Complex II electron transport rate, State 2 respiration rate, State 3 respiration rate, Respiratory Control Ratio, and ATP synthesis rate. The method may further comprise assaying the function of mitochondria of a population of livestock animals and correlating the function of the mitochondria of the population with the mitochondrial function and feed efficiency of at least a second head of livestock to obtain predicted feed efficiencies for the members of said population.

In particular embodiments, a method of the invention may comprise ranking members of a population based on predicted feed efficiency. The ranking may be based on predicted Residual Feed Intake. A method of the invention may also further comprise selecting at least a first head of livestock from the population based on such a ranking and breeding the head of livestock with a second head of livestock to obtain a progeny head of livestock. Selecting the first head of livestock may comprise selecting a head of livestock that exhibits a predicted Residual Feed Intake that is less than the average predicted Residual Feed Intake of the members of said population.

In a method of the invention, mitochondrial function may be determined using mitochondria isolated from muscle or blood cells and the measurement of mitochondrial function may be a measurement of ATP synthesis rate. A method of the invention may also further comprise calculating the Residual Feed Intake of the first livestock animal, and correlating the calculated Residual Feed Intake of the first livestock animal with a measurement of the mitochondrial function of the first livestock animal, and/or with the predicted feed efficiency ranking of the first livestock animal. The livestock animal(s) may be bovine animals, such as *Bos taurus* or *Bos indicus* cattle, and may be a head of beef or dairy cattle.

In another aspect, the invention provides a method of breeding livestock based on a desired feed efficiency, comprising the steps of: (a) assaying at least a first candidate head of livestock for mitochondrial function; (b) correlating the mitochondrial function with the mitochondrial function of at least a second head of livestock having a known feed efficiency to obtain a predicted feed efficiency for the candidate head of livestock; (c) selecting a first parent head of livestock having a desired predicted feed efficiency; and (d) breeding the first parent head of livestock with a second parent head of livestock to obtain a progeny head of livestock with an increased probability of having a desired feed efficiency relative to a head of livestock of the same breed as said first parent head of livestock or said second parent head of livestock that has not been selected for feed efficiency. The first candidate head of livestock may be a bovine animal.

In one embodiment, feed efficiency is determined by Residual Feed Intake. In another embodiment, the second parent head of livestock is selected based on mitochondrial function for a desired predicted feed efficiency. In still further embodiments, the second parent head of livestock is selected by a method comprising the steps of: (a) assaying a population of livestock for mitochondrial function; (b) correlating the mitochondrial function with the mitochondrial function of at least a second head of livestock having a known feed efficiency to obtain a predicted feed efficiency for members of the population; and (c) selecting the second parent head of livestock from the population based on said predicted feed efficiency. Mitochondrial function may be determined, for example, based on at least one characteristic selected from the group consisting of oxygen consumption rate, Complex I electron transport rate, Complex II electron transport rate, State 2 respiration rate, State 3 respiration rate, Respiratory Control Ratio, and ATP synthesis rate. The method may further comprise crossing said progeny head of livestock with a third head of livestock to produce a second generation progeny head of livestock. The improved feed efficiency may be a reduced Residual Feed Intake. In one embodiment, the first parent head of livestock is a head of beef cattle.

In yet another aspect, the invention provides a method for estimating the breeding value of a head of livestock, comprising assaying the mitochondrial function of the head of livestock and correlating the mitochondrial function with the mitochondrial function and Expected Progeny Difference of at least a second head of livestock to obtain a predicted Expected Progeny Difference for said head of livestock. In one embodiment, the mitochondrial function is determined based on at least one characteristic selected from the group consisting of oxygen consumption rate, Complex I electron transport rate, Complex II electron transport rate, State 2 respiration rate, State 3 respiration rate, Respiratory Control Ratio, and ATP synthesis rate. In specific embodiments, the head of livestock is a bovine animal, and may be a head of beef or dairy cattle.

DETAILED DESCRIPTION OF THE INVENTION

The inventors have surprisingly found that measurement of the mitochondrial function of livestock such as cattle allows ranking by predicted Residual Feed Intake. In contrast, previous studies of the relationship between mitochondrial function and "feed efficiency" as defined by ratios of weight-gain (G) and feed-consumption (F), e.g. G:F or F:G yielded conflicting results. The techniques of the invention are significant in that they allow selection of a livestock animal such as a head of cattle for breeding or food production purposes based on a measurement of mitochondrial function. With the increasing costs associated with animal breeding and artificial insemination, each head of livestock produced represents a substantial investment of time and money, and the phenotypic calculation of a RFI value for an animal would require additional time and cost. Selection based on a physiologic trait such as mitochondrial function may thus be employed to provide livestock breeders and/or producers an additional management tool, yielding reduced cost and increased production efficiency.

The invention thus provides, in one aspect, a method for improving efficiencies in livestock production. The invention in particular provides methods for predicting the ranked growth pattern of livestock animals by identifying a physiological indicator in the animals that correlates with calculated Residual Feed Intake, a measure of the metabolic feed efficiency of an animal. This allows efficient management of livestock for breeding and production purposes through screening for that physiological indicator.

The invention therefore provides methods for the improvement of beef cattle with respect to feed efficiency as measured by Residual Feed Intake (RFI). It was found that a measurement of mitochondrial function can be correlated with the calculated RFI of a bovine animal. RFI is a robust measure of metabolic efficiency that does not confound measurement of an animal's metabolic efficiency with growth rate, size, or appetite. Thus, a biochemical assay of mitochondrial function may substitute for, or be used in addition to, the costly and time consuming phenotypic calculation of RFI or other methods of determining feed efficiency. This allows development and use of selection tools such as Expected Progeny Differences (EPD) for one or more metabolic efficiency parameters, including mitochondrial function. Mitochondrial function may be assayed by measurements of oxygen consumption, ATP synthesis, State 2 respiration rate, State 3 respiration rate, and respiratory control ratio (RCR), among others. Measurement of mitochondrial function may also be used in conjunction with other known markers, including genetic, phenotypic, and biochemical markers, in order to make management and selection decisions in bovine livestock breeding and production settings.

Another aspect of the present invention is an improved method for livestock selection comprising correlating the phenotypic feed efficiency of an animal with a measurement of the animal's mitochondrial function. In one embodiment of the invention, the calculation of phenotypic feed efficiency may be by phenotypic determination of residual feed intake. The residual feed intake (Koch et al., 1963) may be calculated by methods known in the art, and as described below, for instance, through use of the GrowSafe™ feed management system. In another embodiment, the feed efficiency of the animal is calculated using the Cornell Value Discovery System (www.cvds.cals.cornell.edu/cvds/; Fox et al., 2004), or another method to calculate a feed conversion ratio, although such a ratio may be less accurate or statistically robust than a calculated RFI. Feed efficiency and growth and production data that may be correlated with mitochondrial function measurements for selection or breeding purposes can also be obtained by other methods or management systems known in the art (e.g. U.S. Pat. No. 6,805,075). Livestock selection may be for purposes of breeding, or for production of food such as beef or dairy products.

In one embodiment, a measurement of the animal's mitochondrial function may be made by biochemical testing of the enzymatic function of mitochondria isolated from muscle cells. In another embodiment, the mitochondria may be isolated from blood cells such as lymphocytes. In accordance with the invention any assay which sorts and identifies cattle based upon differences in mitochondrial function may be used and is specifically included within the scope of this invention. Non-limiting examples of such assays include oxygen consumption, State 2 respiration rate (oxygen consumption in isolated mitochondria in the presence substrate and absence of ADP), State 3 respiration rate (ADP-stimulated oxygen consumption), State 4 respiration rate (oxygen consumption by isolated mitochondria in the absence of ADP or any metabolic poisons or inhibitors), acceptor control ratio (ACR: ratio of State 3 to State 2 respiration rates), respiratory control ratio (RCR; ratio of State 3 respiration rate to State 4 respiration rate), ADP:O (ratio of added ADP to atomic oxygen consumed during oxidative phosphorylation of ADP to ATP), and hydrogen peroxide ($H_2O_2$) production.

One aspect of the present invention comprises a method for predicting the RFI of an animal based on a measurement of its mitochondrial function, prior to, or in the absence of, a calculation of its phenotypic RFI. Thus, a measurement of mitochondrial function may substitute for a calculation of phenotypic feed efficiency, such as by calculation of RFI, for the purpose of making selection decisions.

Another aspect of the present invention comprises a method for using a measurement of mitochondrial function in conjunction with the use of one or more other selection or management tools. These tools may include phenotypic evaluations of animal growth, feed intake, and feed efficiency, including calculation of RFI; ultrasound measurements such as fat depth measurements, marbling scores, and ribeye area; weight gain and other measurements. These tools may also include other biochemical or genetic tests to characterize an animal's efficiency of growth.

The use of biochemical assays to identify livestock displaying improved feed efficiency will find use in breeding or selecting of livestock produced for slaughter, e.g., for production of meat products, by allowing a reduction in feed use. Costs associated with feeding, including cost of feed and manure and methane production could thus be reduced. Thus, one embodiment of the invention comprises a breeding program directed at enhancement of feed efficiency in livestock breeds, especially beef cattle breeds adapted for meat production. Such techniques have to date been largely lacking for beef cattle. Enhancement of feed efficiency may be noted by a reduced RFI value. The method may also be applied to other bovine animals, including dairy cattle. The availability of this additional selection tool for beneficial livestock traits therefore represents a significant advance. Biochemical assays for mitochondrial function may also be employed in conjunction with other selection tools, including genetic markers such as for growth traits (e.g. Kneeland et al., 2004). Genetic markers to be employed may be either nuclear markers or mitochondrial markers. Breeding records may also be employed to correlate mitochondrial function with RFI or another measure of feed efficiency, phenotypic evaluation, and other biochemical, physiological, and phenotypic tools, allowing development and use of Expected Progeny Differences (EPD) related to mitochondrial function and/or feed efficiency as a tool for livestock production and breeding decisions.

As used herein, the term "Residual Feed Intake" (RFI), sometimes referred to as "net feed efficiency" or "net feed intake", is the difference between actual feed intake and that predicted on the basis of mean requirements for body weight maintenance and level of production. Thus, efficient animals, with an RFI value below zero, have daily feed intakes less than would be predicted given their level of production and body weight.

Most natural populations of animals are genetically quite different from the classical linkage mapping populations. While linkage mapping populations are commonly derived from two-generation crosses between two parents, many natural populations are derived from multi-generation matings between an assortment of different parents, resulting in a massive reshuffling of genes. Individuals in such populations carry a complex mosaic of genes, derived from a number of different founders of the population. Gene frequencies in the population as a whole may be modified by a natural or artificial selection, or by genetic drift (e.g., chance) in small populations. Given such a complex population with superior average expression of a trait, a breeder might wish to (1) maintain or improve the expression of the trait of interest, while maintaining desirable levels of other traits; and (2) maintain sufficient genetic diversity that rare desirable alleles influencing the trait(s) of interest are not lost before their frequency can be increased by selection.

Genetic and biochemical assays may find particular utility in maintaining sufficient diversity in a population while maintaining favorable alleles. For example, one might select a fraction of the population based on favorable phenotype (perhaps for several traits—one might readily employ index selection), then apply genetic or biochemical assays as described herein to this fraction and keep a subset which represent much of the allelic diversity within the population. Strategies for extracting a maximum of desirable phenotypic variation from complex populations remain an important area of breeding strategy. An integrated approach, merging classical phenotypic selection with biochemical and/or genetic marker-based analysis, may aid in identifying valuable genotypes from heterogeneous populations.

The techniques of the invention may be applied, in certain embodiments, in connection with any livestock animal. As used herein, "livestock" generally to animals raised primarily for food. For example, such animals include, but are not limited to, cattle (bovine), sheep (ovine), and pigs (porcine or swine) and the like. In a specific aspect of the invention, the livestock may be a defined as not a poultry animal. As used herein, the term "cow" or "cattle" is used generally to refer to an animal of bovine origin of any age. Interchangeable terms include "bovine", "calf", "steer", "bull", "heifer" and the like. As used herein, the term "pig" is used generally to refer to an animal of porcine origin of any age.

The techniques of the present invention may potentially be used with any bovine, including Bos taurus and Bos indicus cattle. In particular embodiments of the invention, the techniques described herein are specifically applied for selection of beef cattle, as the methods described herein will find utility in maximizing production of animal products, such as meat. As used herein, the term "beef cattle" refers to cattle grown or bred for production of meat or other non-dairy animal products. Therefore, a "head of beef cattle" refers to at least a first bovine animal grown or bred for production of meat or other non-dairy animal products. Examples of breeds of cattle that may be used with the invention include, but are not limited to, Africander, Albères, Alentejana, American, American White Park, Amerifax, Amrit Mahal, Anatolian Black, Andalusian Black, Andalusian Grey, Angeln, Angus, Ankole, Ankole-Watusi, Argentine Criollo, Asturian Mountain, Asturian Valley, Australian Braford, Australian Lowline, Bachaur, Baladi, Barka, Barzona, Bazadais, Beefalo, Beefmaker, Beefmaster, Belarus Red, Belgian Blue, Belgian Red, Belmont Adaptaur, Belmont Red, Belted Galloway, Bengali, Berrendas, Bhagnari, Blanco Orejinegro, Blonde d'Aquitaine, Bonsmara, Boran, Braford, Brahman, Brahmousin, Brangus, Braunvieh, British White, Busa, Cachena, Canary Island, Canchim, Carinthian Blond, Caucasian, Channi, Charbray, Charolais, Chianina, Cholistani, Corriente, Costeño con Cuernos, Dajal, Damietta, Dangi, Deoni, Devon, Dexter, Dhanni, Dølafe, Droughtmaster, Dulong, East Anatolian Red, Enderby Island, English Longhorn, Evolène, Fighting Bull, Florida Cracker/Pineywoods, Galician Blond, Galloway, Gaolao, Gascon, Gelbray, Gelbvieh, German Angus, German Red Pied, Gir, Glan, Greek Shorthorn, Guzerat, Hallikar, Hariana, Hays Converter, Hereford, Herens, Highland, Hinterwald, Holando-Argentino, Horro, Hungarian Grey, Indo-Brazilian, Irish Moiled, Israeli Red, Jamaica Black, Jamaica Red, Jaulan, Kangayam, Kankrej, Kazakh, Kenwariya, Kerry, Kherigarh, Khillari, Krishna Valley, Kurdi, Kuri, Limousin, Lincoln Red, Lohani, Luing, Maine Anjou, Malvi, Mandalong, Marchigiana, Masai, Mashona, Mewati, Mirandesa, Mongolian, Morucha, Murboden, Murray Grey, Nagori, N'dama, Nelore, Nguni, Nimari, Ongole, Orma Boran, Oropa, Parthenais, Ponwar, Piedmontese, Pinzgauer, Qinchuan, Rätien Gray, Rath, Rathi, Red Angus, Red Brangus, Red Poll, Retinta, Rojhan, Romagnola, Romosinuano, RX3, Sahiwal, Salers, Salorn, Sanhe, Santa Cruz, Santa Gertrudis, San Martinero, Sarabi, Senepol, Sharabi, Shorthorn, Simbrah, Simmental, Siri, Slovenian Cika, South Devon, Sussex, Swedish Red Polled, Tarentaise, Telemark, Texas Longhorn, Texon, Tharparkar, Tswana, Tuli, Ukrainian Beef, Ukrainian Grey, Ukrainian Whitehead, Umblachery, Ural Black Pied, Väneko, Vestland Red Polled, Vosges, Wagyu, Welsh Black, White Cáceres, White Park, Xinjiang Brown and Yanbian cattle breeds, as well as animals bred therefrom and related thereto.

The techniques of the present invention may also be applied to dairy cattle breeds such as, among others, Ayrshire, Brown Swiss, Canadienne, Dutch Belted, Guernsey, Holstein, Jersey, Kerry, Milking Devon, Milking Shorthorn, and Norwegian Red as well as animals bred therefrom and related thereto.

Food production using the methods of the present invention includes beef production, production of beef byproducts, and production of one or more dairy products, such as milk and products derived therefrom. Production of inedible beef byproducts may also utilize the methods of the present invention. Selection of one or more head of cattle based on the methods of the present invention for breeding or production purposes may be performed on one or more calves, heifers, bull-calves, steers, cows, or bulls.

Techniques for nucleic acid detection may find use in certain embodiments of the invention. For example, such techniques may find use in scoring individuals for certain genotypes, such as the development of novel genetic markers linked to mitochondrial respiration activities (phenotypes). Such nucleic acid detection techniques may include nucleotide hybridization or PCR™ assays to identify specific marker sequences, and to follow their segregation during a program of bovine breeding and selection.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Animal Management and Statistical Analyses

Forty Angus steers (average initial BW=325.4±23.7 kg) were used to select high and low residual feed intake (RFI) animals. Steers were obtained from a single herd enrolled in the MFA Health Track Beef Alliance, were all of the same sire, and had been previously vaccinated and preconditioned for 45 d before arrival at the University of Missouri Beef Research Farm. The animals were tagged with electronic ID tags (Allflex USA, Inc.; Dallas Ft. Worth Airport, Tex.) upon receipt, for measurement of individual feed intake with the GrowSafe feed intake system (GrowSafe Systems Ltd.; Airdrie, AB Canada; U.S. Pat. No. 6,868,804). Steers were placed on a receiving diet for 14 d to allow for acclimation to the feeding system. Following the acclimation period, steers were fed Trendsetter SLR (MFA, Inc.; Columbia, Mo.) at a rate of 25% Trendsetter SLR and 75% whole corn until they reached 454 kg. At 454 kg, the diet was switched to 12.5% Trendsetter SLR and 87.5% whole corn for the remainder of the experiment. All steers had ad libitum access to both feed and water. Steers were weighed every 21 d and RFI values were calculated for each 21 d period and the entire feeding period. Expected feed intake was calculated by regressing actual intake against ADG and metabolic mid weight (Basarab et al., 2003).

The RFI value for each animal was calculated as the difference between the actual and expected intake. Nine low and eight high RFI steers were selected based on their RFI values and were used for the study of mitochondrial respiration. Calculated RFI is shown in Table 1, along with other production parameters. These 17 steers were transported to the University of Missouri Abattoir where the animals were sacrificed to obtain tissue from the LM (longissimus lumborum muscles) for mitochondrial isolation. Hot carcass weights were documented for each animal and the carcasses were chilled for a 24 hr period at 5° C. Following a 24 hr chill, LM area of each carcass was measured to the nearest 0.01 cm$^2$. Subcutaneous fat thickness at the 12$^{th}$ rib was determined using a USDA preliminary yield grade ruler (USDA, 1997) at an anatomical location perpendicular to the vertebral column and ¾ the distance, caudal the LM. To determine preliminary yield grades, the fat measurements were then adjusted, correcting for any atypical fat distribution.

The data were analyzed using the General Linear Model Procedure (SAS Inst., Inc.; Cary, N.C.) as a completely randomized design. An alpha level of 0.05 was used for the determination of statistical significance. The performance of high and low RFI steers is shown in Table 1.

TABLE 1

Performance of steers with high or low residual feed intake (RFI)

| Variable | Low RFI (n = 9) | High RFI (n = 8) |
|---|---|---|
| Initial BW, kg | 332.78 ± 6.75 | 330.17 ± 7.16 |
| Final BW, kg | 566.77 ± 10.00 | 563.07 ± 10.61 |
| ADG, kg/d | 1.48 ± 0.05 | 1.47 ± 0.05 |
| G:F | 0.20 ± 0.01$^a$ | 0.16 ± 0.01$^b$ |
| ADFI, kg/d | 7.40 ± 1.98$^b$ | 8.94 ± 2.10$^a$ |
| Residual feed intake | −0.83 ± 0.09$^b$ | 0.78 ± 0.10$^a$ |
| HCW, kg | 352.17 ± 9.58 | 367.61 ± 10.16 |
| Longissimus dorsi area, cm$^2$ | 76.7 ± 1.15 | 79.74 ± 1.22 |
| Fat thickness over the 12$^{th}$ rib, cm | 2.16 ± 0.15 | 1.92 ± 0.15 |
| USDA yield grade | 4.27 ± 0.20 | 4.00 ± 0.22 |

$^{a,b}$Means within a row lacking a common superscript differ (P < 0.001).
BW: Body weight
HCW: Hot carcass weight
ADG: Average daily gain
G:F: Gain to feed ratio A further analysis was also made, comparing the performance of steers with high, mid or low residual feed intake. The results are presented in Table 2 below.

TABLE 2

Additional analysis of performance of steers with high, mid or low residual feed intake (RFI)

| Variable | Low RFI | Mid RFI | High RFI | SEM |
|---|---|---|---|---|
| Initial BW, kg | 282.20 | 312.05 | 293.56 | 16.23 |
| Final BW, kg | 514.47 | 540.07 | 518.26 | 21.77 |
| ADG, kg/d | 1.39 | 1.36 | 1.34 | 0.06 |
| G:F | 0.17$^a$ | 0.14$^b$ | 0.13$^b$ | 0.004 |
| ADFI, kg/d | 8.39$^b$ | 9.89$^a$ | 10.82$^a$ | 0.38 |
| Residual feed intake | −1.24$^c$ | 0.24$^b$ | 1.35$^a$ | 0.19 |
| HCW, kg | 316.67 | 331.52 | 328.86 | 13.30 |
| Longissimus dorsi area, cm$^2$ | 74.09 | 80.65 | 78.17 | 2.61 |

TABLE 2-continued

Additional analysis of performance of steers with high, mid or low residual feed intake (RFI)

| Variable | Low RFI | Mid RFI | High RFI | SEM |
|---|---|---|---|---|
| Fat thickness over the 12$^{th}$ rib, cm | 1.32 | 1.43 | 1.27 | 0.24 |
| USDA yield grade | 3.00 | 2.83 | 3.17 | 0.25 |

$^{a,b}$Means within a row lacking a common superscript differ (P < 0.01).
BW: Body weight
HCW: Hot carcass weight
ADG: Average daily gain
G:F: Gain to feed ratio G:F and ADFI were both significantly lower and greater respectively for the high RFI steers, which consumed 1.54 kg more feed per day than the low RFI steers. Carcass composition as assessed by LM (Longissimus lumborum muscle) area, fat thickness over 12$^{th}$ rib, HCW, and USDA yield grade were not significantly different between the high and low RFI groups.

Example 2

Isolation of Mitochondria from Skeletal Muscle

All steps were performed at 0-4° C. unless otherwise stated. Between 4-10 g of LM tissue was taken with a scalpel, weighed, added to a centrifuge tube containing 30 ml of ice cold medium 1 (100 mM sucrose; 10 mM EDTA; 100 mM tris-HCl; 46 mM KCl; pH 7.4) and placed on ice. 1 mL Nagarase solution (8 mg Nagarase/1 mL distilled water) was added and the contents of the tube was placed on a shaker/mixer. The tube was incubated at room temperature (25° C.) for 5 minutes with intermittent mixing throughout the incubation period. The contents of the centrifuge tube were then poured into a Potter-Elvenhjem vessel with Teflon pestle of 0.16 mm clearance for homogenization. Seven complete passes were made with the Teflon pestle. The contents were then poured back into the centrifuge tubes and placed on ice for 5-minutes with interval shaking/mixing of the tubes. The resulting homogenate was centrifuged at 1,000-×g for 10 minutes. The supernatant was poured into a high-speed centrifuge tube and the pellet was discarded. The supernatant was centrifuged at 10,000-×g for 15 minutes, and supernatant was discarded. The resulting mitochondrial pellets were resuspended and washed in 10 mL of Medium 1 with 1 mL BSA (5 mg BSA/1 mL in distilled water). The pellet was then centrifuged at 10,000×g for 15 minutes to collect the pellets, and supernatant was discarded. The resulting pellets were resuspended in 20 mL of incubation medium 2 (230 mM mannitol; 70 mM sucrose; 20 mM tris-HCl; 5 mM KH2PO4; pH 7.4) and centrifuged at 8,000-×g for 15 minutes. The resulting pellets were resuspended in 2.0 mL of incubation medium 2 and placed on ice for subsequent studies. Mitochondrial protein was determined by the Coomassie Plus protein assay kit (Pierce Biotechnology, Inc.; Rockford, Ill.). Measurements of mitochondrial function in high or low RFI steers is shown in Table 3.

Example 3

Mitochondrial Oxygen Consumption Measurement

Oxygen consumption (expressed in nmol/min/mg mitochondrial protein) was measured with a with a Clark-type oxygen probe, e.g. YSI model 5300 biological oxygen monitor (YSI, Inc.; Yellow Spring, Ohio), in duplicate. All measurements were completed within 3 hours of isolation. Measurements were performed in a 30° C. circulating water bath.

3 mL of air-equilibrated RCR buffer, (220 mM d-mannitol; 70 mM sucrose; 2 mM HEPES; 3 mM $KH_2PO_4$; pH 7.0) is placed in the prepared standard probe sample chamber of the oxygen monitor. All air is removed from the sample chamber, and the monitor is calibrated to 21%. Aliquots (0.3 mL) of the muscle mitochondrial mixture are added via syringe to the reaction vessel containing 3 mL of RCR reaction buffer. The mitochondrial solution was allowed to equilibrate, substrate was then added to the chamber: either 100 µL of a 0.5M glutamate solution and 10 µL of a 0.5M malate solution (for stimulation of complex I respiration); or 100 µL of a 0.5 M succinate solution (for stimulation of complex II respiration).

The oxygen consumption curve was allowed to decrease in a linear fashion (unprimed or basal rate (state 2 respiration)). Then 10 µL of ADP (50 mM solution) was added and the reaction allowed to run until all the ADP was utilized (state 3 respiration). Once ADP becomes limiting, the curve levels out to its unprimed or basal rate. The slope was allowed to return (state 4 respiration) and then another 10 µL of ADP was added to achieve state 3 respiration. Steps were repeated until all oxygen was consumed. ADP:O ratio was calculated according to the methods of Eastbrook (1967).

Example 4

Lymphocyte Isolation

Blood was collected in a CPT Vacutainer. The tube was inverted 8-10 times to mix anticoagulant, and stored upright at room temperature until centrifugation (within 2 hours). The tube was inverted several times before centrifuging at 1500-1800 RCF in a swinging bucket centrifuge for 20-30 minutes at 18-25° C. Half of the plasma was removed and discarded. Cells were suspended by pipetting and cells/plasma were collected into a 15 mL centrifuge tube. Alternatively the tube can be gently inverted 5-10 times and stored until collection up to 24 hours later.

Phosphate Buffered Saline (PBS; (0.137M NaCl, 0.0027M KCl, 0.0022M $KH_2PO_4$, 0.0097M $Na_2HPO_4$ Anhydrous, pH 7.4)) was added to bring the volume to 13 mL and the tube is mixed by inverting 5 times. The tube was centrifuged for 15 minutes at 300 RCF, and supernatant was removed. Cells were resuspended in a 10 ml volume of PBS, mixed by inverting 5 times, centrifuged for 10 minutes at 300 RCF, and supernatant was removed.

Cells were suspended in 2 mL of storage medium (50% MEM, 40% Fetal bovine serum, 10% DMSO) and stored at −80° C. Alternatively, one may suspend fresh cells in 5 mL MEM (Modified Eagle's Medium) for measurement of ATP synthesis.

Example 5

Lymphocyte Isolation and ATP Determination

A. Cell Incubation and Number

Frozen cells were resuspended in 5 mL of MEM, pelleted by centrifuging at 2000×g for 10 min, washed twice with 5 mL of sucrose medium (0.25M Sucrose; 5 mM Tris; 2 mM; pH 7.4), centrifuged at 2000×g for 10 min, and resuspended in 2.5 mL incubation buffer (150 mM KCl; 25 mM Tris; 2 mM EDTA; 10 mM $KH_2PO_4$; pH 7.4 with 0.1% BSA; 1 mM ADP; and 80 µg/mL digitonin) and divided into 5 500 µL aliquots, and resuspended by pipetting or vortexing. One aliquot was reserved to determine cell number. Cells were then incubated with 10 µL of substrate (100 mM Glutamate or 100 mM Succinate) at 37° C. for 0, 5, 15, and 30 minutes. 17.5 uL 1.6M perchloric acid was added to stop the reaction and cells were centrifuged at 13,000×g for 10 minutes to pellet cell debris. Supernatant was removed to a new tube for the determination of ATP concentration, and 25 uL 1.6M NaOH was added to adjust pH to ~7.8.

To determine cell number, 50 µL of cells was added to 50 µL of PBS. 50 µL of 0.4% trypan blue was added, cells were incubated for 5 min. Blue cells were counted with a hemocytometer to determine cell number.

B. ATP Concentration (Using Sigma FL-AA Kit)

ATP assay mix was dissolved in 5 mL sterile water, and incubated on ice 1 hr. ATP dilution buffer was dissolved in 50 mL sterile water. ATP assay mix was diluted 1:25 with ATP dilution buffer (100 µL in 2.5 mL buffer), a 100 µl sample was added to well and then 100 µl ATP assay reagent was added. The plate was then sealed and read in luminometer.

Example 6

Analysis of Hydrogen Peroxide Production in Respiring Mitochondria

The production of hydrogen peroxide by mitochondria isolated from steers selected to have a high or low RFI was measured using the procedures of Bottje et al. (2002) with modifications. Hydrogen peroxide was measured using the dichloroflourescin diacetate probe (Molecular Probes, Inc.; Eugene, Oreg.) in a 96-well plate fluorimeter (Fluoroskan Ascent; Thermo Electron Corporation, Vantaa, Finland). Mitochondria (0.05 to 0.1 mg protein) were incubated with 52 µM dichloroflourescin diacetate, 64 µL buffer (145 mM KCl, 30 mM HEPES, 15 mM $KH_2PO_4$, 3 mM MgCl, 0.1 mM EGTA, pH 7.4), 10 U superoxide dismutase, and either 10 mM glutamate or succinate. Samples were incubated at 37° C. for 40 min with fluorescence measured every 5 min. Hydrogen peroxide production is calculated from a standard curve and is expressed as nmol $H_2O_2$ generated $min^{-1}$ mg of mitochondrial $proteins^{-1}$. Hydrogen peroxide production is indicative of electron leakage in respiring mitochondria.

TABLE 3

Respiratory function of skeletal muscle mitochondria from steers with high or low residual feed intake (RFI)

| Variable[1] | Glutamate | | Succinate | |
|---|---|---|---|---|
| | Low RFI (n = 9) | High RFI (n = 8) | Low RFI (n = 9) | High RFI (n = 8) |
| State 2 respiration | 98.00 ± 10.19[a] | 62.78 ± 9.53[b] | 109.45 ± 8.05[a] | 77.35 ± 8.05[b] |
| State 3 respiration | 275.17 ± 27.77[a] | 182.87 ± 27.77[b] | 482.90 ± 44.83[a] | 344.33 ± 44.83[b] |
| State 4 respiration | 84.68 ± 4.97 | 79.72 ± 4.97 | 155.47 ± 16.51 | 133.67 ± 16.51 |
| ACR | 3.11 ± 0.20 | 2.68 ± 0.22 | 4.62 ± 0.28 | 3.93 ± 0.28 |

TABLE 3-continued

Respiratory function of skeletal muscle mitochondria from steers with high or low residual feed intake (RFI)

| Variable[1] | Glutamate | | Succinate | |
|---|---|---|---|---|
| | Low RFI (n = 9) | High RFI (n = 8) | Low RFI (n = 9) | High RFI (n = 8) |
| RCR | $3.09 \pm 0.25^a$ | $2.28 \pm 0.25^b$ | $3.84 \pm 0.19^a$ | $2.50 \pm 0.19^b$ |
| ADP:O | $2.02 \pm 0.11$ | $1.80 \pm 0.11$ | $1.92 \pm 0.06$ | $1.76 \pm 0.06$ |
| $H_2O_2$ production | $4.16 \pm 0.43^a$ | $2.77 \pm 0.46^b$ | $13.95 \pm 1.95^a$ | $6.20 \pm 2.25^b$ |
| State 2 respiration/ $H_2O_2$ Production | $22.46 \pm 2.37$ | $20.42 \pm 2.37$ | $11.17 \pm 2.63$ | $9.42 \pm 2.81$ |

[1]ACR = acceptor control ratio (State 3/State 2), RCR = respiratory control ratio (State 3/State 4), ADP:O = adenosine diphosphate to oxygen consumption ratio, $H_2O_2$ production is presented as nmol $H_2O_2$ produced min.$^{-1}$ mg mitochondrial protein$^{-1}$, State 2, 3 and 4 respiration data are presented as nmol $O_2$ consumed min.$^{-1}$ mg mitochondrial protein$^{-1}$.
$^{a,b}$Means within a row lacking a common superscript differ (P < 0.05).

An analysis was also made comparing respiratory function of skeletal muscle mitochondria from steers with high, mid or low residual feed intake. The results are presented in Table 4 below.

TABLE 4

Respiratory function of skeletal muscle mitochondria from steers with high, mid or low residual feed intake (RFI)

| Variable[1] | Glutamate | | | | Succinate | | | |
|---|---|---|---|---|---|---|---|---|
| | Low RFI | Mid RFI | High RFI | SEM | Low RFI | Mid RFI | High RFI | SEM |
| State 2 respiration | $65.05^a$ | $46.73^b$ | $37.84^b$ | 6.56 | $95.67^a$ | $74.62^b$ | $56.36^c$ | 5.86 |
| State 3 respiration | $165.17^a$ | $138.29^{a,b}$ | $116.11^b$ | 13.46 | $265.78^a$ | $214.48^a$ | $129.42^b$ | 34.57 |
| State 4 respiration | 68.67 | 68.97 | 69.15 | 9.81 | 86.40 | 84.96 | 69.76 | 7.13 |
| ACR | 3.08 | 3.22 | 3.16 | 0.29 | 2.70 | 2.71 | 2.41 | 0.23 |
| RCR | $2.80^a$ | $2.46^a$ | $1.72^b$ | 0.16 | $2.77^a$ | $2.44^a$ | $2.03^b$ | 0.18 |
| ADP:O | 2.52 | 2.35 | 2.26 | 0.17 | 1.94 | 1.86 | 2.00 | 0.12 |
| $H_2O_2$ production | $0.39^a$ | $0.19^b$ | $0.13^b$ | 0.08 | $7.90^a$ | $3.40^b$ | $1.75^b$ | 0.94 |
| State 2 respiration/ $H_2O_2$ production | 246.33 | 294.84 | 217.85 | 20.29 | 19.20 | 13.14 | 20.86 | 8.85 |

[1]ACR = acceptor control ratio (State 3/State 2), RCR = respiratory control ratio (State 3/ State 4), ADP:O = adenosine diphosphate to oxygen consumption ratio, $H_2O_2$ production is presented as nmol $H_2O_2$ produced min.$^{-1}$ mg mitochondrial protein$^{-1}$, State 2, 3 and 4 respiration data are presented as nmol $O_2$ consumed min.$^{-1}$ mg mitochondrial protein$^{-1}$.
$^{a,b}$Means within a row lacking a common superscript differ (P < 0.05).

As seen in the tables above, analysis of respiratory function of mitochondria isolated from the LM of high and low RFI steers shows that, when mitochondria were provided with either glutamate or succinate, there was no significant difference in ACR or ADP:O ratios among steers grouped for differing RFI. The respiratory control ratio (RCR) of low RFI steers was significantly greater than that of high RFI steers. A greater respiratory control ratio results from a greater degree of coupling between respiration and oxidative phosphorylation, and suggests increased efficiency of electron transfer. Thus, mitochondria from high RFI animals, with a lower RCR, would be expected to demonstrate more electron leak and hence $H_2O_2$ production than those from low RFI animals. However, mitochondria isolated from high RFI steers produced significantly less hydrogen peroxide, indicative of electron leak, than those from low RFI steers. Because electron leak is a function of respiration rate (Chance et al, 1979), $H_2O_2$ production was also expressed as a ratio to State 2 respiration rate. No difference between high and low RFI steers in the amount of electron leak was observed when $H_2O_2$ production was expressed as a ratio to State 2 respiration rate. Thus, mitochondrial function as measured by $H_2O_2$ production was not impaired in high RFI steers. Instead the flux of electrons through the electron transport chain appears to be impaired Example 7

Measurement of Plasma Glucose and Insulin Concentration

Blood was collected by jugular venipuncture one week before slaughter into vacutainers containing EDTA as an anticoagulant (Becton, Dickinson and Company; Franklin Lakes, N.J.). Samples were collected in the morning before the animal's first major feeding event. The blood samples were centrifuged at 2,200×g for 15 min, the plasma was decanted and frozen at −20° C. until further analysis.

Plasma glucose was determined using a colorimetric glucose oxidase kit (Thermo Electron Corporation; Louisville, Colo.) according to the manufacture's instructions. Plasma concentrations of insulin were quantified using a specific, double-antibody, equilibrium radioimmunoassay as described by Elsasser et al. (1986) with some modifications. Preparation of bovine insulin (Sigma-Aldrich Co.; St Louis, Mo.) for iodination and for standard curve material was via the method of Sodoyez et al. (1975) for preparation of zinc free insulin. Ten µg of zinc free bovine insulin was then solubilized in 50 µl $H_2O$, combined with 500 µCi $^{125}$I—Na, and incubated in the presence of 100 µg of iodogen (Pierce Biotechnology, Inc., Rockford, Ill.) for 6 min with gentle mixing.

Recovery of the mono-iodinated form of $^{125}$I-bovine insulin was achieved by differential elution from a 10 ml Sep-Pak C18 Cartridge as previously described by Deleo (1994) as follows. The Sep-Pak C18 Cartridge was initially washed with 10 ml of 50% (v/v) acetonitrile containing 50 mM triethylamine solution (pH adjusted to pH 3 with phosphoric acid), followed by 10 ml of deionized H$_2$O before addition of the iodination mixture. The cartridge was then washed sequentially with: a) 5 ml of 0.4 M phosphate buffer pH 7.4, b) 10 ml of 29% (v/v) acetonitrile containing 50 mM triethylamine, c) 5 ml of 10% (v/v) acetonitrile containing 0.2 M ammonium acetate, pH 5.5, and finally d) 5 ml of 50% (v/v) acetonitrile containing 0.2 M ammonium acetate, pH 5.5. This final fraction was collected and diluted to 25,000 cpm per 100 µl of assay buffer (0.1% gelatin, 0.01 M EDTA, 0.9% NaCL, 0.01 M PO$_4$, 0.01% sodium azide, 0.1% Tween-20, pH 7.1). Guinea pig anti-bovine insulin antisera (Elsasser et al., 1986) was diluted to a final tube dilution of 1:167,000 in assay buffer. Standard concentrations of zinc free bovine insulin (0.064 to 40 ng/tube) and increasing volumes of a bovine plasma pool (25 to 300 µl) were added to assay tubes in quadruplicate and the total volume balanced to 300 µl per tube with assay buffer.

All plasma samples (100 µl aliquots) to be analyzed were assayed in triplicate. All components were then incubated at 4° C. for 24 h. The antigen-antibody complex was then precipitated following a 15-min, 22° C. incubation with 100 µL of a precipitated sheep-anti-guinea pig second antibody. The second antibody complex was then precipitated by centrifugation at 3,000 g for 30 min and the supernatant discarded by aspiration. Assay tubes containing the precipitate were counted for 1 min on a LKB1275 gamma counter. Standards and plasma aliquots of the bovine plasma pool were linear (log/logit transformation; $r^2$=0.98) and parallel over a mass of 0.064 to 40 ng/tube and a plasma volume of 25 to 300 µL. Total specific binding was 38%, the minimum detectable concentration was 0.064 ng/tube, percentage recovery of mass was 98.1%, and the inter- and intra-assay CV were 5.2 and 6.8% respectively.

A reduced supply of substrate to the mitochondria could affect mitochondrial respiration rates. Plasma glucose and insulin concentrations were measured as an indicator of glucose metabolism and substrate availability to the mitochondria. Plasma glucose and insulin concentrations are shown in Table 5.

TABLE 5

Blood parameters of steers with high or low residual feed intake (RFI)

| Variable | Low RFI (n = 9) | High RFI (n = 8) |
|---|---|---|
| Plasma glucose, mg/dL | 86.44 ± 3.84[b] | 101.12 ± 4.07[a] |
| Plasma insulin, ng/mL | 9.19 ± 1.01 | 11.10 ± 1.07 |
| Ratio of glucose to insulin | 10.04 ± 1.27 | 10.32 ± 1.35 |

[a,b]Means within a row lacking a common superscript differ (P < 0.05).

High RFI steers were observed to have greater (P<0.05) plasma glucose concentrations than low RFI steers. However, plasma insulin concentrations and the ratio of glucose to insulin did not differ between the high and low RFI steers. Plasma insulin values are greater than those reported in the literature (Yambayamba et al., 1996; Hersom et al., 2004) due to the measurement of plasma insulin values with a bovine specific insulin assay. The greater plasma glucose is a result of the greater intake of the high RFI steers, however, glucose metabolism does not seem to be altered because the ratios of glucose to insulin were similar between the high and low RFI steers. It appears that glucose metabolism or availability does not alter mitochondrial respiration rates.

Example 8

Utilizing Mitochondrial Function in Calculating an Expected Progeny

Difference Estimate

Expected progeny differences (EPDs) provide estimates of the genetic value of an animal as a parent, and have been calculated for bovine animals (e.g breeds of cattle). Specifically, differences in EPDs between two individuals of the same breed predict differences in performance between their future offspring when each is mated to animals of the same average genetic merit. EPDs are calculated for birth, growth, maternal, and carcass traits and are reported in the same units of measurement as the trait (normally pounds).

EPDs for various traits are reported by most major beef breed associations, and are calculated using all known information on a particular animal. This information includes performance data (i.e., weight records) on the animal itself, information from its ancestors (sire and dam, grandsire, great grandsire, maternal grandsire, etc.), collateral relatives (brothers and sisters), and progeny (including progeny that are parents themselves). Measurement of mitochondrial function may also be included as a performance parameter in calculating the EPD of an animal. These performance records are adjusted for such factors as age and sex of the animal, and age of the dam prior to inclusion in EPD databases. These adjustment factors allow performance records to be fairly compared in the analysis. Additionally, genetic merit of mates is accounted in evaluating progeny information. Therefore, progeny records are not influenced by superior or inferior mates. The statistical analysis used for EPD calculation also accounts for the effects of environment (nutrition, climate, geographical location, etc.) that exist between herds. These environmental effects can be estimated due to the widespread use of artificial insemination (AI). Through AI, the same bull can be used in several herds across the country. These common sires create genetic links between herds with differing environments and serve as the foundation for evaluation of performance data and EPD calculation across herds. For these reasons, animals with published EPDs within a breed may be directly compared regardless of their age and origin.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 6,805,075
U.S. Pat. No. 6,868,804
WO96/35127
WO03/032234
Basarab et al., 2003 *Can J. Anim. Sci* 83:189-204.
Bottje et al. 2002; *Poultry Sci.* 81:546-555.
Brown, D. R., et al., 1988. *J. Anim. Sci.* 66:1347-1354.
Chance et al., 1979. *Physiol. Rev.* 59:527-605.
Crews 2005. *Gen. Mol. Res.* 4:152-165.
Deleo 1994. Ph.D. dissertation. Curtin University of Technology, Australia.
Eastbrook 1967. *Meth. Enzymol.* 10:41-47.
Elsasser et al. 1986. *Domest. Anim. Endocrinol.* 3:277-287.
Fox et al., 2004. Identifying Differences in Efficiency in Beef Cattle. Animal Science Department Mimeo 225. Cornell University, Ithaca, N.Y.
Hazel, L. N. 1943. *Genetics* 28:476.
Herd et al. 2003. *J. Anim. Sci.* 81:E9-E17.
Hersom et al., 2004. *J. Anim. Sci.* 82:2059-2068.
Iqbal et al., 2004. *Poultry Sci.* 83:474-484.
Johnson et al. 2003. *J. Anim. Sci.* 81:E27-E38.
Kneeland et al., 2004. *J. Anim. Sci.* 82:3405-3414.
Koch et al., 1963. *J. Anim. Sci.* 22:486-494.
Lutz and Stahly. 2003. *J. Anim. Sci.* 81 (Suppl.):141 (Abstr.)
Moore et al 2005. *Aust. J Agr Res,* 56:211.
Nkrumah et al. 2004. *J. Anim. Sci.* 82: 2451-2459.
Ojano-Dirain et al., 2004. *J Poultry Sci.* 83:1394-1403.
Sandelin et al., 2004. *J. Anim. Sci.* 82 (Suppl.):416 (Abstr.).
Sodoyez et al. 1975. *J. Biol. Chem.* 250:4268-4277.
USDA, 1997. Official United States Standards for Grading of Carcasses of Beef. Agric. Marketing. Serv. USDA Washington, D. C.
Yambayamba et al., 1996. *J. Anim. Sci.* 74:57-69.

What is claimed is:

1. A method of breeding livestock based on a desired feed efficiency, comprising the steps of:
 (a) assaying at least a first candidate head of livestock for mitochondrial function;
 (b) correlating the mitochondrial function with the mitochondrial function of at least a second head of livestock having a known feed efficiency to obtain a predicted feed efficiency for the candidate head of livestock;
 (c) selecting a first parent head of livestock having a desired predicted feed efficiency; and
 (d) breeding the first parent head of livestock with a second parent head of livestock to obtain a progeny head of livestock with an increased probability of having a desired feed efficiency relative to a head of livestock of the same breed as said first parent head of livestock or said second parent head of livestock that has not been selected for feed efficiency.

2. The method of claim 1, wherein the first candidate head of livestock is a bovine animal.

3. The method of claim 1, wherein the feed efficiency is determined by Residual Feed Intake.

4. The method of claim 1, wherein the second parent head of livestock is selected based on mitochondrial function for a desired predicted feed efficiency.

5. The method of claim 4, wherein the second parent head of livestock is selected by a method comprising the steps of:
 (a) assaying a population of livestock for mitochondrial function;
 (b) correlating the mitochondrial function with the mitochondrial function of at least a second head of livestock having a known feed efficiency to obtain a predicted feed efficiency for members of the population; and
 (c) selecting the second parent head of livestock from the population based on said predicted feed efficiency.

6. The method of claim 1, wherein mitochondrial function is determined based on at least one characteristic selected from the group consisting of oxygen consumption rate, Complex I electron transport rate, Complex II electron transport rate, State 2 respiration rate, State 3 respiration rate, Respiratory Control Ratio, and ATP synthesis rate.

7. The method of claim 1, further defined as comprising crossing said progeny head of livestock with a third head of livestock to produce a second generation progeny head of livestock.

8. The method of claim 1, wherein the improved feed efficiency is a reduced Residual Feed Intake.

9. The method of claim 1, wherein the first parent head of livestock is a head of beef cattle.

\* \* \* \* \*